United States Patent [19]

Collin et al.

[11] Patent Number: 5,224,147
[45] Date of Patent: Jun. 29, 1993

[54] ANGLE INDICATOR FOR X-RAY MACHINE

[76] Inventors: Gene E. Collin; Catherine A. Collin, both of 1715 Cedarbrook Ct., Sycamore, Ill. 60178

[21] Appl. No.: 926,524

[22] Filed: Aug. 10, 1992

[51] Int. Cl.$^5$ .............................................. H05G 1/28
[52] U.S. Cl. .................................. 378/162; 378/163; 378/205; 378/37
[58] Field of Search ............... 378/162, 163, 165, 164, 378/166, 170, 37, 20, 204, 205

[56] References Cited

U.S. PATENT DOCUMENTS

| | | | |
|---|---|---|---|
| 4,259,585 | 3/1981 | Novak et al. | 250/456 |
| 4,727,565 | 2/1988 | Ericson | 378/205 |
| 5,056,523 | 10/1991 | Hotchkiss, Jr. et al. | 378/37 |

Primary Examiner—David P. Porta
Assistant Examiner—Don Wong
Attorney, Agent, or Firm—Robert L. Marsh

[57] ABSTRACT

An angle indicating device is provided for measuring the angle of an X-ray machine and to display the angle on the photographic plate at the time it is exposed to X-rays. The invention includes the combination of a pendulum mounted to maintain a vertical orientation during rotation of the X-ray machine about its horizontal axis, and an indicator for indicating the angle of the X-ray machine relative to a vertical orientation of the pendulum. Furthermore, a scale and a scale indicator, both of which are opaque to X-rays is provided to project the read out of the angle indicator upon the photographic plate.

10 Claims, 2 Drawing Sheets

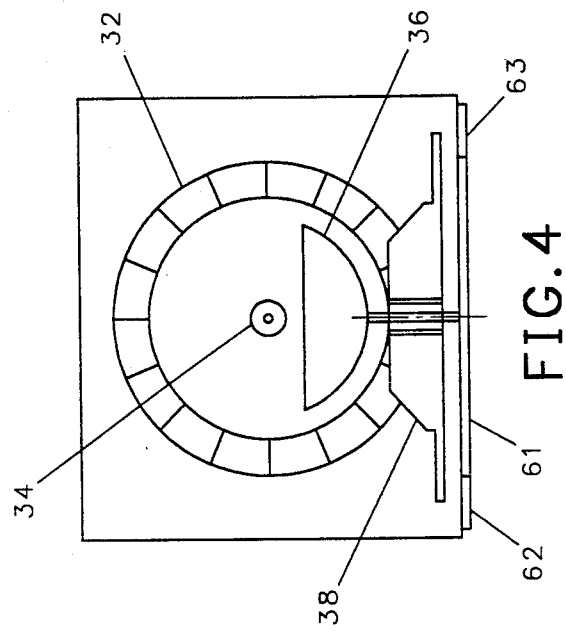
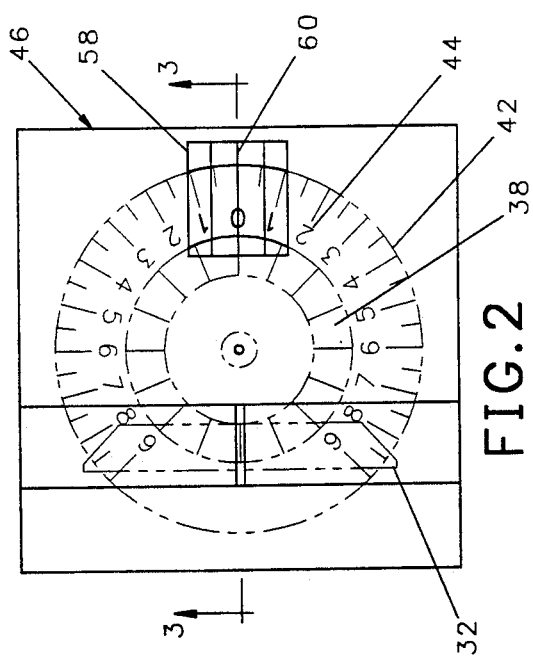
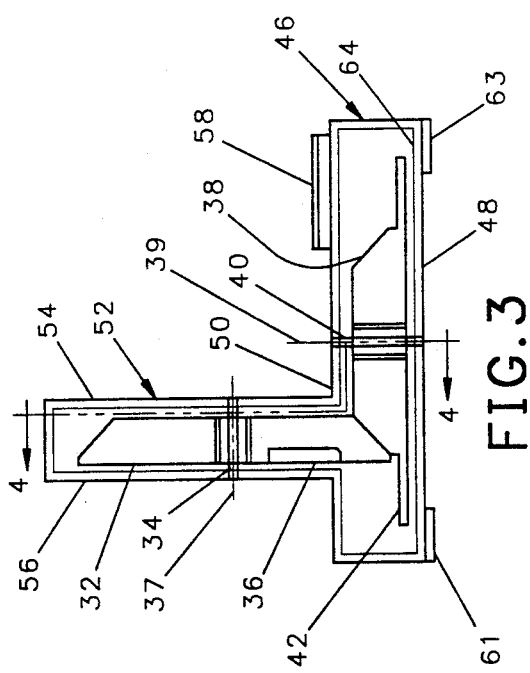

ANGLE INDICATOR FOR X-RAY MACHINE

The present application relates to a device to record on the photographic plate the angle at which an X-ray machine is operated, and specifically to record the angle at which a mammography machine is operated.

BACKGROUND OF THE INVENTION

In the course of taking certain X-rays, as is in the case of mammograms, it is necessary for the operator to record the angle at which the X-ray is taken in order that subsequent X-rays of the same patient may be taken at the same angle. The unique physical features of each individual are different, and as a result the most desirable angle at which mammograms are taken are different from individual to individual. In order to study changes in breast material of a patient over a period of time, each mammogram of a given patient must all be taken at the same angle, and therefore the angle at which each mammogram is taken must be recorded.

Mammogram machines consist of an X-ray gun which projects a ray through a paddle and a film holder assembly between which the patient's breast is positioned, and the photographic plate is positioned below the paddle. The X-ray gun and the paddle and the film holding assembly are held in fixed relationship to each other on what is generally referred to as a "C-arm", and the C-arm, including the gun and connected paddle and film holder assembly, is rotatable around a horizontal axis such that mammograms of a breast may be taken at any angle.

Presently, mammogram machines are provided with an angular scale surrounding the horizontal shaft in which the C-arm is mounted. The operator visually reads the angle of the C-arm on each mammographic exposure and manually notes the angle on the records for each film. A portion of tape, or other material, upon which the angle of the C-arm can be written, may also be attached to each film such that the angle of the C-arm is readily ascertainable by examining the film itself.

When several mammograms are taken at a plurality of angles, a technologist may inadvertently interchange the records for mammographic plates and thereby create confusion with the records of a patient. Furthermore, a technologist may inadvertently misread the angle at which a C-arm is positioned during the course of a mammogram, or position the C-arm at an angle different from that intended by the technologist. In any of these cases, the resulting mammograms will be confusing and inhibit the ability of a radiologist to properly diagnose a patient's condition.

The problems which occur with the present method would be overcome if the angle at which a mammogram machine or any other X-ray machine, is operated would be automatically projected upon the photographic plate at the time of its exposure to X-rays.

BRIEF DESCRIPTION OF THE INVENTION

Briefly, the present invention is embodied in an angle indicating device for measuring the angle at which an X-ray machine is operating at the time the photographic plate is exposed to the rays. Typically, X-ray machines include a X-ray gun directed at a photographic plate which is maintained transverse to the direction of the X-ray beam, with the gun and associated plate being mounted on a mounting member adapted to rotate about a horizontal axis.

The present invention includes a pendulum mounted to maintain a vertical orientation during rotation of the mounting member about its horizontal axis. Also, a means for indicating the angle of the mounting member relative to a vertical orientation of the pendulum which includes an angle scale and a scale indicator one of which is movable relative to the other. The scale and indicator are positioned substantially parallel to the photographic plate of the X-ray machine. The parts of the present invention, except for the scale and the indicator are transparent to X-rays, and the scale and the indicator are opaque to X-rays.

In a preferred embodiment of the present invention, the parts are enclosed in a housing having a base adapted to be positioned above and parallel to the photographic plate. The pendulum is a bevel gear pivoted on an axis which is maintained horizontal and has an off center weight such that the bevel gear will maintain a fixed orientation on rotation of the housing about the horizontal axis. A second bevel gear is engaged at a 90 degree angle with the first bevel gear, and rotates about an axis perpendicular to the base of the housing. Attached to the second bevel gear is an angle scale. An indicator in the form of a hair line is fixed on the housing. Both bevel gears and the housing, including the base are transparent to X-rays whereas the scale and indicator are opaque to X-rays.

BRIEF DESCRIPTION OF THE DRAWINGS

The present invention will be better understood by a reading of the following detailed description taken in connection with the accompanying drawing wherein:

FIG. 2 is a greatly enlarged top view of an angle indicator in accordance with the present invention with the interior portion shown in phantom lines;

FIG. 3 is a cross-sectional view of the angle indicator shown in FIG. 2 taken through line 3—3 of FIG. 2; and FIG. 4 is a cross-sectional view of the angle indicator shown in FIG. 2 taken through line 4—4 of FIG. 3.

DETAILED DESCRIPTION OF THE PREFERRED EMBODIMENT

Figure 1:
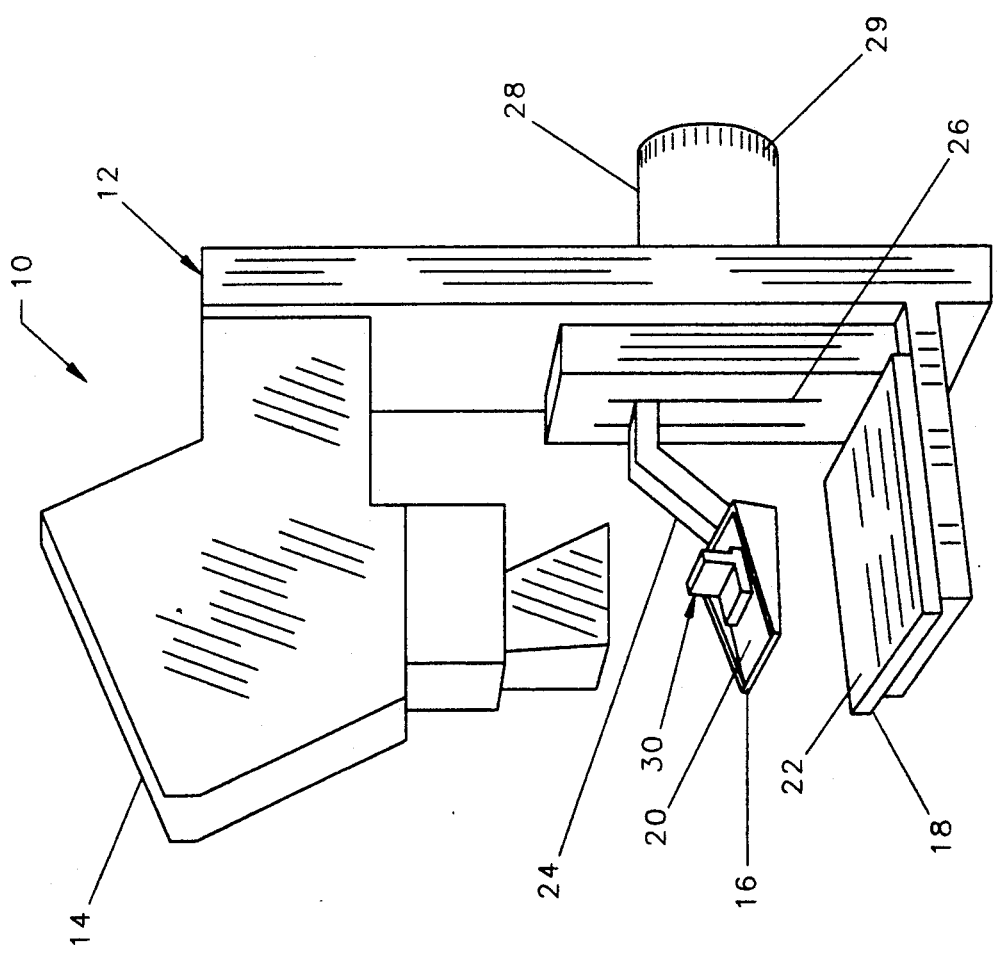
FIG. 1 is an isometric drawing of a C-arm of a mammogram machine including the X-ray gun, paddle, and film holder assembly, and an angle indicator in accordance with the present invention positioned on the paddle thereof.

Referring to FIG. 1, there is shown a typical mammography machine 10, having a C-arm 12 at the upper end of which is an X-ray gun 14 and at the lower end is a paddle 16 and a film holder assembly 18, which retains a photographic plate therein, not shown. The paddle 16 has a plate 20 having parallel upper and lower surfaces which are maintained parallel to the planar upper surface 22 of the film holder assembly 18 and to the photographic plate therein The paddle 16 is fixedly attached to an arm 24 which is slidably mounted in a track 26 such that the paddle 16 may be slidably moved toward or away from the upper surface 22 of the film holder assembly 18. When in use, the breast of a patient is positioned between the undersurface of the plate 20 of the paddle 16 and the upper surface 22 of the film holder assembly 18. The paddle 16, and the upper surface 22 of the film holder assembly 18 are transparent to X-rays and when X-rays are emitted from the gun 14 they will pass through the paddle, the breast material of a patient, the upper surface 22 of the film holder assembly 18 and into the photographic plate therein.

The C-arm 12 is fixedly mounted to a horizontal rotating shaft 27 having an axis 28 on which there is provided an angular index 29. The C-arm 12 is therefore a mounting member for maintaining the gun 14 and paddle 16 and film holder assembly 18 in the desired relation to one another during rotation of the C-arm 12 about the axis of the horizontal shaft 28. The C-arm may be locked into the angle most suitable for any patient, and maintained at that angle by the locking mechanism, not shown, during the taking of a mammogram.

As shown in FIG. 1, there is provided on the paddle 16 of the mammogram machine 10 an angle indicating device 30 in accordance with the present invention.

Referring to FIGS. 2, 3 and 4 there is portrayed an angle indicating device 30 in accordance with the present invention. As shown in FIG. 4, the angle indicating device 30 includes a first bevel gear 32 made of a light weight material such as plastic mounted on a shaft 34, suitably journalled for rotation, and having an off-center weight 36. When the longitudinal axis 37 of the shaft 34 is maintained horizontal, the weight 36 will act as a pendulum around the longitudinal axis 37 of the shaft 34.

A second bevel gear 38 is positioned at 90 degrees to the first bevel gear 32 mounted on a second shaft 40 which is also suitably journalled for rotation and the primary longitudinal axis 39 of which is co-planar with the longitudinal axis 37 of shaft 34 of the first bevel gears 32. An annular flange 42 surrounds the outer circumference of the second bevel gear 38 on which is imprinted an angle scale 44. The first bevel gear 32 and second bevel gear 38 are enclosed in a housing 46 which has a substantially planar base 48 which serves as the bottom of the housing 46. The housing 46 further has an upper surface 50 parallel to the base 48 between which the shaft 40 of the second bevel gear 38 is rotatably retained perpendicular thereto to permit rotation of the second bevel gear 38 and of the flange 42 in a plane parallel to the base 48. The housing further includes a vertical portion 52 having opposing parallel sides 54, 56 which rotatably retain perpendicular thereto the shaft 34 of the first bevel gear 32.

A transparent lens 58 is provided in the upper surface 50 above the scale 44 and the lens 58 includes an angle indicator cross hair 60 positioned above and transverse to a portion of the scale 44 on the annular flange 42 of the second bevel gear 38.

In the preferred embodiment, the housing 46 of the device 30 is retained on the upper surface of the paddle 16 during rotation of the C-arm 12 by a magnetic strip 61 positioned along a portion of the underside of the base 48 which is not adjacent the angle indicator cross hair 60. The magnetic strip 61 will magnetically attach the angle indicator 30 to a metallic strip, not shown, positioned along the back edge of the paddle 16, and thereby retain the angle indicating device 30 on the paddle 16 during rotation of the C-arm 12 about the axis 28 of the shaft 27. Finally, rubber feet 62, 63 are provided adjacent the forward corners of the underside of the base 48, and the feet 62, 63 have a thickness equal to the thickness of the magnetic strip 61 so as to maintain the housing 46 and base 48 parallel to the upper surface of the paddle 16.

Referring to FIG. 1, when an angle indicating device 30 is positioned on a portion of the paddle 16 of a mammography machine 10 where the base 48 is maintained parallel to the photographic plate, not shown, and the axis 37 of the first bevel gear 32 is parallel to the axis 28 of the shaft 27, the axis 37 of the shaft 34 of the first bevel gear 32 will be maintained in a horizontal orientation for all angles at which the C-arm 12 of the mammography machine 10 is rotated. As a result, the weight 36 on the first bevel gear 32 will act as a pendulum and maintain the first bevel gear 32 in a fixed vertical orientation as the C-arm 12 and the housing 46 of the angle indicating device 30 are angularly rotated about the axis 28 of the shaft 27. It will be apparent, therefore, that upon the rotation of the C-arm 12, the housing 46 of the device 30 will rotate around the axis 37 of the first bevel gear 32 which maintains its vertical orientation and will cause the second bevel gear 38 to be rotated through an arc which is proportional to the angle at which the housing 46 is turned relative to the vertical. During such movement, the annular flange 42 will at all times be in a plane parallel to the plane of the photographic plate, not shown. The scale 44 on the annular flange 42 is adapted to portray the angle at which the base 48 housing 46 is turned relative to the horizontal and the angle indicator cross-hair 60 may be used to accurately read the angle of the base 48 and therefore the angle of the C-arm 12 and the photographic plate, not shown. The operator can visually read the angle by looking through the lens 58 and reading the scale 44 where it is intersected by the cross hair 60.

The present invention further provides that the housing 46, the lens 58 and the flange 42 are transparent to X-rays, however, the scale 44 and the cross-hair 60 are of a material which are opaque to X-rays, such as lead. When the angle indicating device 30 is positioned at the corner or the edge of the paddle 16 as shown in FIG. 1, X-rays emitted from the gun 14 will pass through the transparent portions of the angle indicating device 30, the paddle 16 and the upper surface 22 of the film holder assembly 18 and into the photographic plate below and cast an image of the scale 44 and cross hair 60 onto the edge of the photographic plate. When the photographic plate is then developed, the angle of the base 48 of the angle indicator 30, and therefore the angle of the C-arm 12 itself, will be projected on the photographic plate, not shown.

Although the scale 44 of the present invention is shown as being printed on the annular flange 42, and therefore rotatable upon alteration of the angle of the device 30, the present invention could also be constructed with a transparent annular flange 42 bearing a cross hair which would rotate above a fixed scale printed on the upper surface 64 of the base 48.

Furthermore, although the present invention is portrayed as being enclosed in its own housing 46, the invention could readily be incorporated into the paddle 16, or the film holder assembly 18 of the mammography machine 10. In this a configuration, a separate housing 34 may not be required and portions of the paddle 16 or of the film holder assembly 18 may pivotally support the shafts 34, 40 of the first and second bevel gears 32, 38, respectively. In such a configuration, the axis 37 of shaft 34 of the first bevel gear 32 must be maintained parallel to the axis 28 of the shaft 27 of the C-arm 12, and the plane of the second bevel gear 38 and of the annular flange 42 must be maintained parallel to the plane of the photographic plate, not shown.

In the preferred embodiments, the scale 44 is adapted so that a zero is positioned at the intersection of the cross-hair 60 when the base 48 is in a horizontal orientation. The first bevel gear 32 has forty five teeth and the second bevel gear 38 is smaller and has thirty teeth. As a result, a thirty degree rotation of the C-arm 12 will cause a forty-five degree rotation of the second bevel gear 38, and the scale 44 imprinted on the flange 42 therefor is enlarged. For example, an indicia of thirty degrees will be imprinted on the scale 44 at a position forty-five degrees from the position indicated as zero degrees.

There is therefore disclosed an angle indicating device 30 which is attachable to an X-ray machine, such as a mammography machine, which can be manually read by an operator to provide the angle at Which the machine is positioned, and which will project an image onto the X-ray film upon operation of the machine.

While the present invention has been described in connection with one embodiment, it will be understood by those skilled in the art that many changes may be made without departing from the true spirit and scope of the present invention. Therefore, it is intended by the appended claims to cover all such changes and modifications which come within the true spirit and scope of the invention.

What is claimed is:

1. An angle indicating device for measuring the angle at which an X-ray machine is operated, said X-ray machine being of the type having an X-ray gun directed at a photographic plate retained transverse to the direction of the X-ray beam, in a container having the portions positioned between the photographic plate and X-ray gun transparent to X-rays and further having a mounting member for mounting the X-ray gun and the container for the photographic plate, the mounting member being rotatable about a horizontal axis, said angle indicating device comprising in combination:
    pendulum means mounted for rotation about an axis parallel to the axis of said mounting member,
    angle indicating means parallel to said photographic plate responsive to the movement of said mounting member relative to said pendulum means for indicating the angle between said pendulum means and said mounting member, and
    positions of said angle indicator means made of a material opaque to X-rays so as to project an image of said angle indicator means onto said photographic plate.

2. An angle indicating device in accordance with claim 1 wherein:
    said pendulum means is a first bevel gear having a off-center weight.

3. An angle indicating device in accordance with claim 2 wherein said angle indicator means is a second bevel gear engaged with said first bevel gear at an angle of approximately 90 degrees.

4. An angle indicating device in accordance with claim 3 further comprising a transparent lens over said angle indicator means whereby an operator may visually read said scale on said angle indicator means.

5. An angle indicating device in accordance with claim 1 wherein said angle indicating means comprises a scale and a cross-hair.

6. An angle indicating device for measuring the angle at which an X-ray machine is operated, said X-ray machine being of the type having an X-ray gun directed at a planar transverse photographic plate retained in a container, the portion of said container which is positioned between said X-ray gun and said photographic plate are transparent to X-rays, said container and said X-ray gun mounted on a mounting member being rotatable about a horizontal axis, said angle indicating device comprising in combination:
    a housing having a base adapted to be positioned parallel to the plane of said photographic plate between said gun and said photographic plate,
    pendulum means mounted on said housing for maintaining a vertical orientation during rotation of said housing about an axis parallel to the axis of said mounting member,
    angle indicating means parallel to said base responsive to movement of said pendulum for indicating the angle of said pendulum relative to said base,
    portions of said base adjacent said angle indicator means made of a material transparent to X-rays, and,
    said angle indicating means made of a material opaque to X-rays.

7. An angle indicating device in accordance with claim 6 wherein:
    said pendulum means is a first bevel gear having an off-center weight.

8. An angle indicating device in accordance with claim 7 wherein said angle indicator means is a second bevel gear engaged with said first bevel gear at an angle of approximately 90 degrees.

9. An angle indicating device in accordance with claim 8 further comprising a transparent lens over said angle indicator means whereby an operator may visually read said scale on said angle indicator means.

10. An angle indicating device in accordance with claim 6 wherein said angle indicating means comprises a scale and a cross-hair.

* * * * *